by reaction of an appropriate organo lithium with either the compound of Example 27 or Example 20AY.

Table 40

| Example | $R_6(1)$ | $R_6(3)$ | Wt. S.M. | Wt. Prod. | m.p. (° C.)/Solvent |
|---|---|---|---|---|---|
| 40A | $CH_3$ | $CHOHCH_3$ | 3.0 | 1.09 | 108–111/ether-hexane |
| 40B | $C_6H_5CHOH$* | H | 2.96 | 2.2 | 198–204/$CH_2Cl_2$-heptane |
| 40C | $CH_2=CHCHOH$ | H | 5.92 | 2.07 | 144–146/benzene |
| 40D | $CH_3$ | $CHOHC_6H_5$ | 6.0 | 4.12 | 151–154/acetonitrile |
| 40E | $CH_3$ | $CHOHCH=CH_2$ | 6.0 | 2.88 | 160–165/ethyl acetate |
| 40F | $C_4H_9CHOH$ | H | 5.92 | 2.4 | 75–80/- |
| 40G | $CH_3$ | $C(CH_3)_2OH$ | 2.0 | 0.68 | 184–186/ether-hexane |
| 40H | $C_2H_5CHOH$ | H | 2.96 | 2.62 | 155–156/ether-heptane |

*Phenyl magnesium bromide used as the organo metallic reagent.

Example 41

Reaction of the 2,4,5,6-tetrahydro-1,3,4,6,6-pentamethylcyclopenta[c]pyrrole-4-carbonitriles described in Examples 2, 7, 4A, 4C, 4K, and 8 in an autoclave at 150°–160° C. with an ethanol solution saturated with anhydrous ammonia and anhydrous hydrogen sulfide affords the following compounds of Formula I where, in each instance, $R_1$ and $R_2$ are hydrogen; $R_3$, $R_4$, $R_5$ and $R_6$ are each $CH_3$; and X is S.

Table 41

| Example | $R_7$ |
|---|---|
| 41A | $CH_3$ |
| 41B | $CH_2CH_2CH_2N(CH_3)_2$ |
| 41C | $CH_2CH_2C_6H_5$ |
| 41D | $C_6H_5$ |
| 41E | 2-pyridyl |
| 41F | $CH_2CH_2CSNH_2$ |

Example 42

Reaction of the ethyl 4-carbamoyl-2,4,5,6-tetrahydro-1,3,4,6,6-pentamethylcyclopenta[c]pyrrole-2-acetate described above in Example 20AC with alcoholic sodium hydroxide and isolation of the product from an acid or neutral medium affords 4-carbamoyl-2,4,5,6-tetrahydro-1,3,4,6,6-pentamethylcyclopenta[c]pyrrole-2-acetic acid.

Example 43

Reaction of the 2-(4-carboxyphenyl)-2,4,5,6-tetrahydro-1,3,4,6,6-pentamethylcyclopenta[c]pyrrole-4-carboxamide described above in Example 20BZ with methanol in the presence of a small amount of a mineral acid affords 2-(4-carbomethoxyphenyl)-2,4,5,6-tetrahydro-1,3,4,6,6-pentamethylcyclopenta[c]pyrrole-4-carboxamide.

Example 44

Reaction of the 2-(3-methylmercaptophenyl)-2,4,5,6-tetrahydro-1,3,4,6,6-pentamethylcyclopenta[c]pyrrole-4-carboxamide described above in Example 20CB with one molar equivalent of performic acid in acetone at room temperature affords 2-(3-methylsulfinylphenyl)-2,4,5,6-tetrahydro-1,3,4,6,6-pentamethylcyclopenta[c]pyrrole-4-carboxamide.

Example 45

Reaction of 2-(3-methylmercaptophenyl)-2,4,5,6-tetrahydro-1,3,4,6,6-pentamethylcyclopenta[c]pyrrole-4-carboxamide described above in Example 20CB with two molar equivalents of performic acid in acetone at room temperature affords 2-(3-methylsulfonylphenyl)-2,4,5,6-tetrahydro-1,3,4,6,6-pentamethylcyclopenta[c]pyrrole-4-carboxamide.

Example 46

Reaction of the 2-phenyl-2,4,5,6-tetrahydro-1,3-diformyl-4,6,6-trimethylcyclopenta[c]pyrrole-4-carboxamide described above in Example 20AB with two molar equivalents of perbenzoic acid in acetone at room temperature affords 2-phenyl-2,4,5,6-tetrahydro-4,6,6-trimethylcyclopenta[c]pyrrole-4-carboxamido-1,3-dicarboxylic acid.

Example 47

Reaction of the 2-phenyl-2,4,5,6-tetrahydro-4,6,6-trimethylcyclopenta[c]pyrrole-4-carboxamido-1,3-dicarboxylic acid described above in Example 46 with methanol in the presence of a small amount of a mineral acid affords dimethyl 2-phenyl-2,4,5,6-tetrahydro-4,6,6-trimethylcyclopenta[c]pyrrole-4-carboxamido-1,3-dicarboxylate.

Example 48

Reaction of 1-phenyl-2,4,5,6-tetrahydro-1,3,4,6,6-pentamethylcyclopenta[c]pyrrole-4-carbonitrile with one molar equivalent of diisobutyl ammonium hydride in tetrahydrofuran, and, without isolation of the product, oxidation of the resulting material with oxygen affords 2-phenyl-2,4,5,6-tetrahydro-1,3,4,6,6-pentamethylcyclopenta[c]pyrrole-4-carboxamide.

Data obtained on oral administration in rats of the compounds of Formula I in the anti-secretory and the reserpine-induced anti-ulcer tests are given in terms of the % increase in the pH of gastric fluid over control animals and the % reduction in ulcer score over control animals. Doses are expressed in mg./kg., and the compounds are identified by the Example number above where they are disclosed.

| Example | Dose | % pH Increase | % Reduction Ulcer Score |
|---|---|---|---|
| 20 | 25 | 9 | 60 |
|  | 50 | 50 | 60 |
|  | 100 | 84 | 100 |
|  | 200 | 96 | 100 |
| 20A |  | Inactive | Inactive |
| 20B | 100 | 20 | 40 |
| 20C | 100 | 24 | 0 |
| 20D | 100 | 7 | 0 |
| 20E | 100 | 4 | 0 |
| 20F | 12.5 | 41 | — |
|  | 25 | 52 | 73 |
|  | 50 | 75 | 100 |
|  | 100 | 100 | 100 |
| 20G | 25 | — | 40 |
|  | 50 | 55 | 60 |
|  | 100 | 93 | — |
|  | 100 | 95 | 100 |

PROCESS FOR THE PRODUCTION OF 2-NITROBUTYLMORPHOLINE

This is a continuation of copending application Ser. No. 741,175, filed Nov. 12, 1976.

BACKGROUND OF THE INVENTION

This invention relates to an improved process for the production of 2-nitrobutylmorpholine.

More particularly, this invention relates to an improved process for the production of 2-nitrobutylmorpholine by reacting 1-nitropropane, morpholine and formaldehyde.

The prior known processes for the production of 2-nitrobutylmorpholine, Senkus, U.S. Pat. No. 2,474,791 teach the production of 2-nitroisobutylmorpholine from the reaction of a nitroalcohol and a cyclic secondary amine (2-nitro-2-methyl-1-propanol and morpholine). The second process taught by Senkus is the reaction of formaldehyde with the cyclic secondary amine (morpholine) which in turn is reacted with a secondary nitroparaffin (2-nitropropane). A variation of the first method as taught by Senkus is the reaction of formaldehyde with the nitroparaffin (2-nitropropane) to produce the nitroalcohol which in turn is reacted with the cyclic secondary amine (morpholine) which process is hereinafter called the morpholine addition method.

A by-product from the reaction forming 2-nitrobutylmorpholine from 1-nitropropane, formaldehyde and morpholine is 2-nitro-1-butanol. 2-Nitro-1-butanol is difficult to separate from the 2-nitrobutylmorpholine product and as a nitroalcohol can react violently with bases such as morpholine. The 2-nitro-1-butanol formed contaminates and reduces the yield and purity of 2-nitrobutylmorpholine. Another disadvantage inherent in the prior processes is that they require excess 1-nitropropane and morpholine to drive the reaction to completion. Generally a 20% excess 1-nitropropane and 1% excess morpholine over formaldehyde are required. The use of such excesses is uneconomical and the excess of both reactants adds to the contamination of the product. The use of excess reactants reduces the efficiency of the process in that more reactants are required to drive the reaction to completion than actually react and effort is needed to separate the reactants from the finished products. The prior processes require strict controls during the reaction in order to produce 2-nitrobutylmorpholine efficiently. In the morpholine addition process strict controls are maintained on the addition of the morpholine. Longer addition times than three hours or interruptions during the addition step produces more of the by-product 2-nitro-1-butanol.

SUMMARY OF THE INVENTION

It is an object of this invention to provide an improved process for the production of 2-nitrobutylmorpholine.

Another object of this invention is to provide an improved process for the production of 2-nitrobutylmorpholine by reacting 1-nitropropane, morpholine and formaldehyde.

A further object of this invention is to provide an improved process for the production of 2-nitrobutylmorpholine wherein the product produced is of greater purity than that from prior known processes.

Other objects of this invention will be apparent to those skilled in the art from the disclosure herein.

An improvement has been found in the process for the production of 2-nitrobutylmorpholine from the reaction of 1-nitropropane, morpholine and formaldehyde in about a 1:1:1 molar ratio. According to the prior process, the 1-nitropropane and formaldehyde were mixed together at about 50°–60° C. then morpholine was added over a 1–3 hour addition time. According to the present invention, the improvement comprises mixing 1-nitropropane and morpholine, heating to about 55°–60° C., then adding formaldehyde over about a 3–4 hour period, holding the reaction mixture at about 55°–60° C. for about a 2–3 hour period to make a total addition/holding period of at least six hours, cooling the reaction mixture to form a two phase oil/aqueous system and concentrating the oil layer to 2-nitrobutylmorpholine by removing excess water and 1-nitropropane.

DETAILED DISCUSSION

The process of this invention is an improvement over the prior processes for the production of 2-nitrobutylmorpholine. The prior processes teach mixing (1) 2-nitro-2-methyl-1-propanol and morpholine, or (2) mixing morpholine and formaldehyde then adding 1-nitropropane or (3) mixing formaldehyde and 1-nitropropane then adding morpholine. The improved process of this invention mixes the reactants, 1-nitropropane and morpholine, then adds formaldehyde. The unexpected result was obtained that the process of this invention produces a product of greater purity than the prior processes. The process produces less contaminating by-products and is less sensitive to longer addition times or interruptions during the addition step. The process of this invention produces a product, 2-nitrobutylmorpholine, that is essentially free from the major contaminant of the prior known processes, 2-nitro-1-butanol.

1-Nitropropane and morpholine are charged to a reaction vessel equipped with a jacket for heating or cooling. An excess of 5–20% 1-nitropropane, preferably 10–15% over a 1:1 molar ratio to formaldehyde is charged to the reaction vessel. The preferred range of 1-nitropropane is sufficient to produce high yields, but small enough to leave little unreacted 1-nitropropane to contaminate the product, 2-nitrobutylmorpholine. Also, the 10–15% excess 1-nitropropane does not produce any appreciable amount of 2-nitro-1-butanol by-product.

The morpholine is added to the reaction vessel preferably in about a 1% excess over the 1:1 molar ratio to formaldehyde. Amounts less than 1% excess produce 2-nitro-1-butanol and amounts greater than 1% decrease the product purity by leaving unreacted morpholine in the end product.

The mixture of 1-nitropropane and morpholine is heated to between 55°–60° C. Temperatures lower than 55° C. do not produce 2-nitrobutylmorpholine efficiently. Temperatures greater than 60° C. are not detrimental to product composition, but can lead to high coloration of the product.

Formaldehyde, 37%, is added to the vessel with constant agitation and maintaining the temperature within the preferred 55°–60° C. range. The formaldehyde is added over a 2½–6 hour addition period. Preferably, the formaldehyde is added in about 3–4 hours addition time. Addition times of less than 2½ hours produce, 4,4'-(2-ethyl-2-nitrotrimethylene)dimorpholine and addition times of longer than 6 hours have no appreciable effect on product formation. Longer addition times than 6 hours and interruptions during addition produce no

Example 34

A solution of 9.0 g. (0.03 mole) of 2-phenyl-2,4,5,6-tetrahydro-1,3,4,6,6-pentamethylcyclopenta[c]pyrrole-4-carboxylic acid (described in Example 31) in 50 ml. of anhydrous tetrahydrofuran, and the solution treated with 5.4 g. (0.033 mole) of carbonyldiimidazole. The mixture was then treated with a solution of 2.9 g. (0.03 mole) of aniline in 25 ml. of tetrahydrofuran, the solution stirred at room temperature for twenty-four hours, and then taken to dryness in vacuo. The residue was partitioned between water and diethyl ether, and the ether layer was washed with brine, then dried and taken to dryness leaving 10.8 g. of a solid residue which was recrystallized twice from methanol to give 4.7 g. of 1-(2-phenyl-2,4,5,6-tetrahydro-1,3,4,6,6-pentamethylcyclopenta[c]pyrrol-4-yl carbonyl)imidazole, m.p. 134°–136° C.

Example 35

A mixture of 29.6 g. (0.1 mole) of 2-phenyl-2,4,5,6-tetrahydro-1,3,4,6,6-pentamethylcyclopenta[c]pyrrole-4-carboxamide (described in Example 20F) and 0.10 g. of cupric acetate monohydrate in 300 ml. of a 4:6 methanol/benzene mixture was stirred under two atmospheres of oxygen for twenty hours. The resulting black solution was taken to dryness, and the residual dark semi-solid was dissolved in 300 ml. of methylene dichloride and the solution washed with water, then with saturated brine, charcoaled, filtered and taken to dryness. The residue was recrystallized twice from methanol to give 14.1 g. of a mixture of 2-phenyl-1-methoxymethyl-2,4,5,6-tetrahydro-3,4,6,6-tetramethylcyclopenta[c]pyrrole-4-carboxamide and 2-phenyl-3-methoxymethyl-2,4,5,6-tetrahydro-1,4,6,6-tetramethylcyclopenta[c]pyrrole-4-carboxamide, m.p. 181°–193° C.

Example 36

A mixture of 10 g. (0.032 mole) of 2-phenyl-1-formyl-2,4,5,6-tetrahydro-3,4,6,6-tetramethylcyclopenta[c]pyrrole-4-carboxamide (described in Example 27) and 1.0 g. of 10% palladium-on-charcoal in 100 ml. of 2-(2-ethoxy)ethoxyethanol was heated to reflux under nitrogen for eight hours and then cooled and allowed to stand at ambient temperature for about twelve hours. The catalyst was removed by filtration, the filtrate poured into water and the mixture extracted with benzene. The benzene extracts, after washing, drying and evaporation to dryness, gave a yellow gum which was triturated with ether and recrystallized from benzene to give 0.9 g. of 2-phenyl-2,4,5,6-tetrahydro-3,4,6,6-tetramethylcyclopenta[c]pyrrole-4-carboxamide, m.p. 186°–190° C.

Example 37

2-Phenyl-1-formyl-2,4,5,6-tetrahydro-4,6,6-trimethylcyclopenta[c]pyrrole-4-carboxamide (described in Example 20AY) (2.96 g., 0.01 mole) dissolved in 30 ml. of benzene and 120 ml. of tetrahydrofuran was reacted with 5.7 ml. (0.012 mole) of a 2.1 molar benzene solution of diethyl aluminum cyanide using the procedure described above in Example 17. The product was isolated as an amorphous foam which solidified on trituration with benzene. There was thus obtained 2.75 g. of 2-phenyl-1-(hydroxycyanomethyl)-2,4,5,6-tetrahydro-4,6,6-trimethylcyclopenta[c]pyrrole-4-carboxamide as the hemi-benzene solvate, slowly decomposes at 120° C., resolidifies and melts again at 142° C.

Example 38

To a solution of 1.0 g. (0.003 mole) of 2-phenyl-1-hydroxymethyl-2,4,5,6-tetrahydro-4,6,6-trimethylcyclopenta[c]pyrrole-4-carboxamide (described in Example 26A) in 7 ml. of pyridine was added 570 mg. (0.004 mole) of 4-methylbenzoyl chloride. The reaction mixture was refrigerated for two days, poured into saturated sodium bicarbonate solution, extracted with methylene dichloride and the organic extracts dried and evaporated to dryness to give 1.3 g. of residue which was recrystallized from ethyl acetate to give 696 mg. of 2-phenyl-1-(4-methylbenzoyloxymethyl)-2,4,5,6-tetrahydro-4,6,6-trimethylcyclopenta[c]pyrrole-4-carboxamide, m.p. 200°–204° C.

Using the procedure described in Example 38, the following compounds of Formula I, where in each case $R_1$, $R_2$ and $R_6$ (3-position) are each hydrogen, $R_3$, $R_4$ and $R_5$ are each $CH_3$ and $R_7$ is $C_6H_5$, were prepared from 2-phenyl-1-hydroxymethyl-2,4,5,6-tetrahydro-4,6,6-trimethylcyclopenta[c]pyrrole-4-carboxamide and acetic anhydride or succinic anhydride.

Table 38

| Example | $R_6(1)$ | Wt. S.M. | Wt. Prod. | m.p. (° C.)/Solvent |
|---|---|---|---|---|
| 38A | $CH_3COOCH_2$ | 2.0 | 1.46 | 174–176/ethyl acetate |
| 38B | $HOOC(CH_2)_2COOCH_2$ | 2.0 | 0.9 | 152–154/ethyl acetate-hexane |

Example 39

To a solution of 1 g. (0.0025 mole) of 2-phenyl-1-(3-carboxypropionyloxymethyl)-2,4,5,6-tetrahydro-4,6,6-trimethylcyclopenta[c]pyrrole-4-carboxamide (described in Example 38B) in 10 ml. of tetrahydrofuran at 0°–5° C. was added anhydrous ammonia by passing the gas over the surface of the solution. The mixture was diluted with ether and the gummy solid which separated solidified on scratching to give 1.0 g. of the corresponding ammonium salt, m.p. 116°–118° C.

Example 40

To a suspension of 2.96 g. (0.01 mole) of 2-phenyl-1-formyl-2,4,5,6-tetrahydro-4,6,6-trimethylcyclopenta[c]pyrrole-4-carboxamide (described in Example 20AY) in 50 ml. of tetrahydrofuran was added 12.9 ml. of a 0.16 molar solution of methyl lithium while cooling the mixture. After stirring for one hour at 0°–5° C. and for two hours at ambient temperature, the mixture was poured into ice/aqueous ammonium chloride and extracted with methylene dichloride. The extracts, on drying and evaporation to dryness, gave crude product which was recrystallized from methylene dichloride-heptane to give 1.91 g. of 2-phenyl-1-(1-hydroxyethyl)-2,4,5,6-tetrahydro-4,6,6-trimethylcyclopenta[c]pyrrole-4-carboxamide, m.p. 135°–145° C.

Using a procedure similar to that described in Example 40 above, the following compounds of Formula I where in each case $R_1$ and $R_2$ are each hydrogen, $R_3$, $R_4$ and $R_5$ are each $CH_3$ and $R_7$ is $C_6H_5$ were prepared

TABLE I-continued

Reaction Parameters and Vanderbilt G.C. Analysis[1]

| | | | Vanderbilt G.C. Area % Compositions Elution Times (Minutes) | | | | | | |
|---|---|---|---|---|---|---|---|---|---|
| | | | .4–5 | 1.0 | 2.0 | 3.6 | 5.2 | 6.2 | 8.4 |
| Example Number | HCHO Addition Time | Concentration Method | Identities | | | | | | |
| | | | Nitro-paraffins | Morpholine | 2-Nitro-1-Butanol | (2) | (3) | Unknown | (4) |
| 11 | 3 | $H_2O$ Azeotrope[6] | 0.80 | — | — | 0.90 | 98.2 | — | 0.20 |

[1]Examples 2–9 were with 20% excess 1-nitropropane, Examples 10 and 11 were with 10% excess 1-nitropropane
[2]4-(2-methyl-2-nitropropyl)morpholine
[3]2-nitrobutylmorpholine
[4]4,4'-(2-ethyl-2-nitrotrimethylene)dimorpholine.
[5]3 hour addition rate with 3 hour feed interruption at midpoint of feed.
[6]Reaction $H_2O$ layer not separated.

What is claimed is:

1. In the process for the production of 2-nitrobutylmorpholine from 1-nitropropane, morpholine and formaldehyde in about a 1.05–1.2:1.01:1 molar ratio the improvement comprising the steps of (a) mixing 1-nitropropane, and morpholine, (b) heating the mixture to about 55°–60° C., (c) then adding formaldehyde over about a 3–4 hour period, (d) holding the mixture at about 55°–60° C. for about a 2–3 hour period to make a total addition/holding period of at least six hours, (e) cooling the reaction mixture to form a two-phase oil-aqueous system, (f) collecting and discarding the water (upper) layer and (g) concentrating the oil layer to 2-nitrobutylmorpholine by removing excess water and 1-nitropropane.

2. The process of claim 1 wherein the formaldehyde is added over about a 3 hour period or more.

3. The process of claim 1 wherein said concentrating of the oil layer is performed by steam sparging.

4. The process of claim 1 wherein said concentrating of the oil layer is performed by extraction with water.

5. The process of claim 1 wherein said formaldehyde is added over a four-hour period and said mixture is held at 55°–60° C. for a two-hour period.

* * * * *

UNITED STATES PATENT AND TRADEMARK OFFICE
CERTIFICATE OF CORRECTION

PATENT NO. : 4,140,855
DATED : February 20, 1979
INVENTOR(S) : Robert W. Shelton It is certified that error appears in the above-identified patent and that said Letters Patent are hereby corrected as shown below:

Column 5, line 11, "2-nitropropy)" should read
-- 2-nitropropyl) --

Signed and Sealed this

Fifth Day of June 1979

[SEAL]

Attest:

RUTH C. MASON
Attesting Officer

DONALD W. BANNER
Commissioner of Patents and Trademarks